(12) United States Patent
Pfeffinger et al.

(10) Patent No.: US 6,525,223 B2
(45) Date of Patent: Feb. 25, 2003

(54) PREPARATION OF SECONDARY AMINES FROM NITRILES

(75) Inventors: Joachim Pfeffinger, Ludwigshafen (DE); Michael Hüllmann, Bensheim (DE); Arthur Höhn, Kirchheim (DE); Frank Funke, Mannheim (DE); Frank Ohlbach, Düsseldorf (DE); Till Gerlach, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/026,900

(22) Filed: Dec. 27, 2001

(65) Prior Publication Data

US 2002/0128513 A1 Sep. 12, 2002

(30) Foreign Application Priority Data

Jan. 5, 2001 (DE) .......................... 101 00 314

(51) Int. Cl.$^7$ ............................ C07C 209/48
(52) U.S. Cl. .................. 564/490; 564/415; 564/448; 564/493
(58) Field of Search ................ 564/415, 448, 564/490, 493

(56) References Cited

U.S. PATENT DOCUMENTS 4,311,859 A * 1/1982 Murtha et al. .............. 564/491
4,444,898 A * 4/1984 Schwartz et al. ............ 502/62

FOREIGN PATENT DOCUMENTS

WO 91/10641 * 7/1991 ......... C07C/209/48

* cited by examiner

Primary Examiner—Brian Davis
(74) Attorney, Agent, or Firm—Keil & Weinkauf

(57) ABSTRACT

Secondary amines of the formula (II)

$$(X-CH_2-)_2NH \qquad (II)$$

where

X is a $C_{1-20}$-alkyl, $C_{2-20}$-alkenyl or $C_{3-8}$-cycloalkyl group which may be unsubstituted or substituted by $C_{1-20}$-alkyl, $C_{3-8}$-cycloalkyl, $C_{4-20}$-alkylcycloalkyl, $C_{4-20}$-cycoalkylalkyl, $C_{2-20}$-alkoxyalkyl, $C_{6-14}$-aryl, $C_{7-20}$-alkylaryl, $C_{7-20}$-aralkyl, $C_{1-20}$-alkoxy, hydroxy, $C_{1-20}$-hydroxyalkyl, amino, $C_{1-20}$-alkylamino, $C_{2-20}$-dialkylamino, $C_{2-12}$-alkenylamino, $C_{3-8}$-cycloalkylamino, arylamino, diarylamino, aryl-$C_{1-8}$-alkylamino, halogen, mercapto, $C_{2-20}$-alkenyloxy, $C_{3-8}$-cycloalkoxy, aryloxy and/or $C_{2-8}$-alkoxycarbonyl, are prepared by reacting nitriles of the formula (III)

$$X-CN \qquad (III)$$

with hydrogen at from 20 to 250° C. and pressures of from 60 to 350 bar in the presence of an Rh-containing catalyst comprising from 0.1 to 5% by weight, based on the total weight of the catalyst, of Rh on a support to give mixtures of primary amines of the formula (I)

$$X-CH_2-NH_2 \qquad (I)$$

and secondary amines of the formula (II)

$$(X-CH_2-)_2NH \qquad (II)$$

and returning at least part of the primary amines separated from the mixtures obtained to the reaction.

7 Claims, No Drawings

PREPARATION OF SECONDARY AMINES FROM NITRILES

This application claims priority from GER. 10/00319-5 filed Jan. 5, 2001.

The present invention relates to a process for preparing secondary amines from nitriles over a rhodium catalyst.

Processes for preparing amines from nitriles over particular rhodium catalysts are known.

U.S. Pat. No. 3,117,162 relates to the hydrogenation of nitriles, in which coupling reactions are said to be minimized. Rhodium-containing catalysts can be used, and the hydrogenation is carried out at pressures in the range from 1 to 50 atmospheres. For example, 5% of rhodium on carbon is used as catalyst. In addition to primary amines, secondary amines are also obtained, cf. Table V. The reaction is carried out in an inert solvent.

U.S. Pat. No. 5,574,189 relates to the hydrogenation of nitriles for preparing amines. In particular, secondary amines are to be prepared. While mainly multimetal catalysts are described, a catalyst comprising 1% of Rh on $Al_2O_3$ is also described for comparison, cf Table V. The reaction is carried out at 500 psi (34 bar). Primary, secondary and also tertiary aliphatic amines are obtained.

It is an object of the present invention to provide a process for preparing secondary amines in high yields and selectivities by selecting nitrites with hydrogen in the presence of catalysts.

In particular, symmetrical secondary amines are to be prepared.

We have found that this object is achieved by a process for preparing secondary amines of the formula (II)

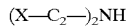 (II)

where

X is a $C_{1-20}$-alkyl, $C_{2-20}$-alkenyl or $C_{3-8}$-cycloalkyl group which may be unsubstituted or substituted by $C_{1-20}$-alkyl, $C_{3-8}$-cycloalkyl, $C_{4-20}$-alkylcycloalkyl, $C_{4-20}$-cycloalkylalkyl, $C_{2-20}$-alkoxyalkyl, $C_{6-14}$-aryl, $C_{7-20}$-alkylaryl, $C_{7-20}$-aralkyl, $C_{1-20}$-alkoxy, hydroxy, $C_{1-20}$-hydroxyalkyl, amino, $C_{1-20}$-alkylamino, $C_{2-20}$-dialkylamino, $C_{2-12}$-alkenylamino, $C_{3-8}$-cycloalkylamino, arylamino, diarylamino, aryl-$C_{1-8}$-alkylamino, halogen, mercapto, $C_{2-20}$-alkenyloxy, $C_{3-8}$-cycloalkoxy, aryloxy and/or $C_{2-8}$-alkoxycarbonyl, by reacting nitriles of the formula (III)

 (III)

with hydrogen at from 20 to 250° C. and pressures of from 60 to 350 bar in the presence of an Rh-containing catalyst comprising from 0.1 to 5% by weight, based on the total weight of the catalyst, of Rh on a support to give mixtures of primary amines of the formula (I)

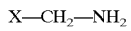 (I)

and secondary amines of the formula (II)

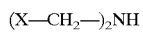 (II)

and returning at least part of the primary amines separated from the mixtures obtained to the reaction.

The amount of primary amines returned to the reaction is preferably selected so that it corresponds essentially to the amount of primary amines present after the reaction. This is made possible by use of the catalyst employed according to the present invention.

The process of the present invention makes it possible to prepare secondary amines in high yields, in particular without formation of primary amines which have to be discharged from the process.

According to the present invention, it has been found that the use of a catalyst as defined above for the reaction of nitriles with hydrogen to form secondary amines can also lead to a longer operating life or long-term stability of the catalyst The catalysts used according to the present invention contain from 0.1 to 5% by weight, preferably from 0.3 to 3% by weight, particularly preferably from 0.5 to 1% by weight, of rhodium, based on the total weight of the catalyst.

In addition, they can further comprise from 0.1 to 10% by weight, preferably from 0.1 to 5% by weight, particularly preferably from 0.2 to 1% by weight, based on the total weight of the catalyst, of at least one additional metal selected from among those of groups IB and VIII of the Periodic Table of the Elements, cerium and lanthanum. It is possible to use one additional metal or a mixture of a plurality of additional metals. In this case, preference is given to copper, platinum, palladium and mixtures thereof, particularly preferably platinum.

Rh is preferably the only active component present in the catalyst. The catalyst particularly preferably consists of Rh on the support.

As support, it is possible to use all known suitable supports. For example, the support may be selected from among activated carbon, silicon carbide and metal oxides. As metal oxides, preference is given to using zeolites, aluminum oxide, silicon dioxide, titanium dioxide, zirconium dioxide, zinc oxide, magnesium oxide or mixtures thereof, which may optionally be doped with alkali metal oxides and/or alkaline earth metal oxides. Particular preference is given to using γ-aluminum oxide, silicon dioxide, zirconium dioxide or titanium oxide or mixtures thereof, in particular γ-$Al_2O_3$ and $ZrO_2$. The supports can be used in any form, for example as extrudates, pellets or tablets.

Particular preference is given to a catalyst comprising from about 0.5 to 1.0% by weight of Rh, based on the total weight of the catalyst, on γ-$Al_2O_3$ or $ZrO_2$ as support.

The catalysts can be produced by generally known methods, for example by impregnating the support with solutions of compounds of the metals used.

The supports can, for example, be coated with metal precursors. Suitable metal precursors are metal salts such as nitrates, nitrosyl nitrates, halides, carbonates, carboxylates, acetylacetonates, chloro complexes, nitrito complexes and amine complexes of rhodium. Preference is given to nitrates, chlorides, chloro complexes and amine complexes, in particular nitrates. Application of the precursors is preferably carried out by impregnation. The precursors of the metals (if a plurality of metals is present) can be applied simultaneously or in succession. The order in which the active components are applied can be chosen freely.

Preference is given to impregnating the support material with a solution of a rhodium salt in a suitable solvent, preferably in water. In the impregnation of the support material with the rhodium-containing solution, the amount of solution used can be calculated so that it corresponds to from about 80 to 100% of the water uptake capacity of the support material. The concentration of rhodium in the solution is then chosen so that the desired loading of the support material with rhodium is achieved. The impregnated support material is dried at from 50 to 200° C., preferably from 100 to 140° C. Drying can be carried out with the support material in motion or static and for a period of from 0.5 to 10 hours, preferably from 4 to 6 hours. The calcination of the dried catalyst is carried out at from 300 to 800° C., preferably from 400 to 600° C., and can likewise be carried out with the catalyst in motion or static. The calcined catalyst has to be reduced before use in the synthesis, and this can be achieved by treatment with hydrogen at from 100 to 300° C., preferably from 180 to 220° C., at atmospheric pressure for a period of from 2 to 20 hours, preferably from 8 to 14 hours, after installation of the catalyst in the synthesis reactor.

Further methods of producing the catalysts used according to the present invention are known to those skilled in the art and include vapor deposition, sputtering and coprecipitation.

The surface area, the pore volume and the pore size distribution of the catalyst are not critical within wide ranges.

The process of the present invention is carried out batchwise or preferably continuously at from 20 to 250° C., preferably from 50 to 200° C., particularly preferably from 100 to 140° C., and pressures of from 60 to 350 bar, preferably from 70 to 200 bar, particularly preferably from 70 to 120 bar, in pressure apparatuses such as autoclaves or preferably in a tube reactor. The pressure is preferably the hydrogen pressure in the reactor. When using a tube reactor, the catalyst employed can also be present in a fixed bed.

The reaction is preferably carried out in the liquid phase in the upflow or downflow mode, particularly preferably in the upflow mode. In particular, preference is given to carrying out the reaction without use of ammonia.

The WHSV over the catalyst, based on the nitrile used, is preferably from 0.1 to 2 kg/(1 h), in particular about 0.6 kg/(1 h). It is possible to recirculate part of the liquid reaction product (in addition to the primary amine) to the reaction.

The process of the present invention can be carried out in the absence of solvents or in the presence of solvents such as water, methanol, ethanol, tetrahydrofuran, methyl tert-butyl ether or N-methylpyrrolidone. The nitrile of the formula (III) can be dissolved in the solvent. Preference is given to carrying out the reaction in the absence of a solvent The amines of the formulae (I) and (II) obtained in the process of the present invention can be separated from the reaction mixture and purified in a manner known per se, for example by distillation.

For example, it is possible to rectify the reaction mixture to give a stream comprising pure secondary amine and a stream comprising primary amine and recirculate at least part of the stream comprising the primary amine to the synthesis. The amount of primary amine recirculated is preferably such that the primary amine neither accumulates nor is depleted in the reaction mixture.

The nitriles reacted in the process of the present invention have the formula (III),

X—CN (III)

where
X is a $C_{1-20}$-alkyl, $C_{2-20}$-alkenyl or $C_{3-8}$-cycloalkyl group which may be unsubstituted or substituted by $C_{1-20}$-alkyl, $C_{3-8}$-cycloalkyl, $C_{4-20}$-alkylcycloalkyl, $C_{4-20}$-cycloalkylalkyl, $C_{2-20}$-alkoxyalkyl, $C_{6-14}$-aryl, $C_{7-20}$-alkylaryl, $C_{7-20}$-aralkyl, $C_{1-20}$-alkoxy, hydroxy, $C_{1-20}$-hydroxyalkyl, amino, $C_{1-20}$-alkylamino, $C_{2-20}$-dialkylamino, $C_{2-12}$-alkenylamino, $C_{3-8}$-cycloalkylamino, arylamino, diarylamino, aryl-$C_{1-8}$-alkylamino, halogen, mercapto, $C_{2-20}$-alkenyloxy, $C_{3-8}$-cycloalkoxy, aryloxy and/or $C_{2-8}$-alkoxycarbonyl,
X is preferably $C_{1-12}$-, particularly preferably $C_{1-8}$-, in particular $C_{1-6}$-, specially $C_{1-4}$-alkyl which may be branched or unbranched but is preferably unbranched. Examples are unbranched radicals made up of 1, 2, 3, 4, 5, 6, 7, 8, 9, 10, 11, 12, 13, 14, 15, 16, 17, 18, 19, 20 methylene units, C(C)—C—C, C—C(C)—C, C—C(C)$_2$—C as structural units. Preferred structural units are C, C—C, C—C—C, C—C—C—C, C—C—C—C—C, C—C(C)—C—C, C—C(C)—C—C, C—C—C(CN)—C—C—C, particularly preferably C, C—C, C—C—C, C—C—C—C.

X can, as indicated above, be substituted. In this case, the number of substituents can be up to the number of replaceable hydrogen atoms in X. Regardless of the type of radical, from 1 to 5, preferably from 1 to 3, in particular 0, 1 or 2, substituents may be present. Possible substituents are:

$C_{1-20}$-alkoxy, preferably $C_{1-8}$-alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy, particularly preferably $C_{1-4}$-alkoxy such as methoxy, ethoxy, n-propoxy, isopropoxy, n-butoxy, isobutoxy, sec-butoxy and tert-butoxy, hydroxy, $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 2-hydroxy-2-propyl and 3-hydroxy-n-propyl, amino, $C_{1-20}$-alkylamino, preferably $C_{1-8}$-alkylamino, particularly preferably $C_{1-4}$-alkylamino such as methylamino, or corresponding aminoalkyl, 1-aminoethyl, 2-aminoethyl, 2-amino-n-propyl and 3-amino-n-propyl, $C_{2-20}$dialkylamino, preferably $C_{2-12}$-dialkylamino, in particular $C_{2-8}$-dialkylamino such as N,N-dimethylamino, N,N-diethlamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropylamino, $C_{3-12}$-azacycloalkyl, preferably $C_{3-8}$-azacycloalkyl, particularly preferably $C_{5-8}$-azacycloalkyl such as pyrrolidine, piperidine, hexahydroazepine, piperazine, N-alkylpiperazine and morpholine, $C_{3-8}$-cycloalkylamino such as cyclopropylamino, cyclobutylamino, cyclopentylamino, cyclohexylamino, cycloheptylamino and cyclooctylamino, preferably cyclopentylamino, cyclohexylamino and cyclooctylamino, particularly preferably cyclopentylamino and cyclohexylamino, $C_{3-8}$-dicycloalkylamino, arylamino such as phenylamino, 1-naphthylamino and 2-naphthylaminio, preferably phenylamino, aryl-$C_{1-8}$-alkylamino, preferably phenyl-$C_{1-8}$-alkylamino, particularly preferably phenyl-$C_{1-4}$-alkylamino such as phenylmethylamino and phenylethylamino, halogen, preferably fluorine, chlorine and bromine, particularly preferably fluorine and chlorine, mercapto, $C_{2-20}$-oxacycloalkyl, preferably $C_{2-8}$-oxacycloalkyl, particularly preferably $C_{2-8}$-oxacycloalkyl such as 2-tetrahydrofuranyl, 3-tetrahydrofuranyl, 2-furanyl and 3-furanyl, $C_{3-8}$-cycloalkoxy such as cyclopropoxy, cyclobutoxy, cyclopentoxy, cyclohexoxy, cycloheptoxy and cyclooctoxy, preferably cyclopentoxy, cyclohexoxy, particularly preferably cyclopentoxy and cyclohexoxy, aryloxy such as phenoxy, 1-naphthoxy and 2-naphthoxy, preferably phenoxy.

There are preferably 0, 1 or 2 substituents which are OH or $C_{2-12}$-, preferably $C_{2-6}$-, in particular $C_{2-4}$-dialkylamino. In particular, the substituents are dimethylamino or OH.

Preferred nitriles of the formula (III) are acetonitrile, propionitrile, isopropionitrile, butronitrile, valeronitrile, petenenitrile, retenenitrile, 3-hydroxypropionitrile, 3-methoxypropionitrile, 3-ethoxypropionitrile, 3-isopropoxypropinitrile, 3 cyclohexoxy-propionitrile, 2-methyl-3-hydroxypropinitrile, 3-methoxy-2-methylpropionitrile, 3-ethoxy-2-methylpropionitrile, 2-methyl-3-propoxypropionitrile, 3-isopropoxy-2-methylpropionitrile, 3-cyclohexoxy-2-methylpropionitrile, 3-methyl-3-hydroxypropinitrile, 3-methoxy-3-methylpropionitrile, 3-ethoxy-3-methylpropionitrile, 3-methyl-3-propionitrile, 3-isopropoxy-3-methylpropionitrile, 3cyclohexoxy-3-methylpropionitrile, 3-aminopropionitrile 3-methylaminopropionitrile, 3-dimethylaminopropionitrile, 3-ethyl-aminopropionitrile, 3diethylaminopropionitrile, 3-propylaminopropionitrile, 3-dipropylaminopropionitrile, 3-isopropylaminopropionitrile, 3-diisopropylaminopropionitrile, 3-cyclohexylaminopropionitrile, 3-dicyclohexylaminopropionitrile, N-(cyanoethyl)-N-methylaniline. Particular preference is given to 3-hydroxypropionitrile, 3-methoxypropionitrile, 3-dimetylaminopropionitrile, 3-diethylaminopropionitrile, 3cyclohexylaminopropionitrile and 3-methylaminopropionitrile, in particular biscyanoethyl ether, bicyanoethylamine, N-methylbiscyanoethylamine, N-ethylbiscyanoethylamine, N-n-propylbiscyanoethylamine, polyisobutylenenitrile, N-polyisobutyleneaminopropionitrile, tricyanoethylamine. 5-aminovaleroitrile, 5-methylaminovaleronitrile, 5-dimethyaminovaleronitrile, 6-aminocapronitrile, 6-methylaminocapronitrile, 6-methylaminocapronitrile, 5-amino-4-methylvaleronitrile, 5-methylamino-4-methylvaleronitrile, 5-dimethylamino4-methylvaleronitrile, 5-ethylamino-4-methylvaleronitrile, 5-dimethylamino-4-methylvaleronitrile, 5 amino-2-methylvaleronitrile, 5-methylamino-2-methylvaleronitrile, 5dimethylamino-2valeronitrile, 5-ethylamino-2-methylvaleronitrile, 5-ethylamino-2-methylvaleronitrile, 4cyanosuberonitrile, acylonitrile.

Very particular preference is given to adiponitrile, 3-dimethylaminopropionitrile (DMAPM) and 3-hydroxypropionitrile, especially DMAPN.

The secondary amines, preferably bis-DMAPA, can be used as hardeners for epoxy resins, catalysts for polyurethanes, intermediates for preparing quaternary ammonium compounds, plasticizers, corrosion inhibitors, textrile assistants, dyes and emulsiflers. Multiply functionalized tertiary amines are also employed for producing plastics, ion exchangers, pharmaceuticals, crop protection agents and pesticides.

The invention is illustrated by the following examples.

EXAMPLE 1

Reference

An electrically heated tube reactor having an internal diameter of 30 mm and a total length of 2.0 m and fitted with a centrally located thermocouple having a diameter of 12 mm is filled with a mixture of 286 g (=500 ml) of the catalyst and 450 ml of stainless steel packing elements. The catalyst comprises 1.0% by weight of Rh on $\gamma$-$Al_2O_3$ as support material and is in the form of extrudates having a diameter of 2 mm and a length of 5–10 mm.

Before the reaction, the catalyst is reduced by means of pure hydrogen at 180° C. under atmospheric pressure for a period of 12 hours.

400 g/h of 3-(dimethylamino)propionitrile (DMAPN), 1.5 kg/h of liquid reaction product and 0.4 standard $m^3$/h of hydrogen are passed through the reactor in cocurrent from the bottom upward. The starting materials are preheated to 120° C. upstream of the reactor. The reactor is maintained at 120° C. and a total pressure of 200 bar.

The mixture leaving the reactor is cooled, part of the liquid is recirculated to the reactor inlet and the remainder is depressurized to atmospheric pressure. Gas-chromatographic analysis of the output from the reactor found 63% by weight of bis(3-dimethylaminopropyl)amine (bis-DMAPA), 29% by weight of 3-dimethylaminopropylamine (DMAPA), 0.3% by weight of DMAPN and 7.7% by weight of various by-products. The conversion of DMAPN was thus 99.7%, the selectivity to bis-DMAPA based on DMAPN used was 62%.

EXAMPLE 2

Reference

The procedure of Example 1 was repeated using 595 g (=500 ml) of a catalyst comprising 0.5% by weight of Rh on $ZrO_2$ as support material. The catalyst was in the form of rings having a diameter of 7 mm, a hole diameter of 3 mm and a thickness of 3 mm.

300 g/h of 3-(dimethylamino)propionitrile (DMAPN), 2.5 kg/h of liquid reaction product and 0.4 standard $m^3$/h of hydrogen are passed through the reactor in cocurrent from the bottom upward. The reactor was operated at 130° C. and a total pressure of 200 bar. A reaction product comprising 69% by weight of bis(3-dimethylaminopropyl)amine (bis-DMAPA), 26% by weight of 3-dimethylaminopropylamine (DMAPA), 0.9% of DMAPN and 4.1% by weight of various by-products was obtained. The conversion of DMAPN was thus 99.1%.

EXAMPLE 3

300 g/h of 3-(dimethylamino)propionitrile (DMAPN), 125 g/h of recovered dimethylaminopropylamine (DMAPA), 1.5 kg/h of liquid reaction product and 0.4 standard m³/h of hydrogen are passed through the reactor of Example 1 in cocurrent from the bottom upward. The reactor was operated at 140° C. and a total pressure of 100 bar. A reaction product comprising 54% by weight of bis(3-dimethylaminopropyl)amine (bis-DMAPA), 35% by weight of 3-dimethylaminopropylamine (DMAPA), 0.1% of DMAPN was obtained. The product mixture was distilled batchwise. The first fraction obtained in this distillation at atmospheric pressure was DMAPA in a purity of 99.5% and a distillation yield of 90% and this was returned to the synthesis. Subsequently, at a total pressure of 50 mbar, bis-DMAPA was obtained in a purity of 99.2% and a distillation yield of 88%. The total molar yield of bis-DMAPA based on DMAPN used is thus, including the distillation, about 67%.

EXAMPLE 4

An electrically heated tube reactor having an internal diameter of 20 mm, a total length of 0.31 m and fitted with a centrally located thermocouple having a diameter of 3 mm is filled with 61 g (=100 ml) of catalyst. The catalyst comprises 0.5% by weight of Rh on $\gamma$-$Al_2O_3$ as support material and is in the form of thin extrudates having a star-shaped cross section and a length of 5–10 mm.

Before the reaction, the catalyst is reduced by means of pure hydrogen at 300° C. under atmospheric pressure for a period of 12 hours.

The flows indicated in Table 1 of 3-(dimethylamino)propionitrile (DMAPN) and dimethylaminopropylamine (DMAPA), 39 g/h of liquid reaction product and 20 l/h of hydrogen are passed through the reactor in cocurrent from the bottom upward. The reactor is maintained at 120° C. and a total pressure of 80 bar.

The mixture leaving the reactor is cooled and depressurized to atmospheric pressure. The product flows indicated in Table 1 of DMAPN, DMAPA and bis-DMAPA are calculated from the gas-chromatographic analysis of the product.

The data in Table 1 show that, under the conditions reported, it is possible to obtain feed ratios of DMAPN to DMAPA in which the DMAPA balance is virtually zero (last column in Table 1). The bis-DMAPA selectivity based on DMAPN is then above 90%.

X is a $C_{1-20}$-alkyl, $C_{2-20}$-alkenyl or $C_{3-8}$-cycloalkyl group which may be unsubstituted or substituted by $C_{1-20}$-alkyl, $C_{3-8}$-cycloalkyl, $C_{4-20}$-alkylcycloalkyl, $C_{4-20}$-cycloalkylalkyl, $C_{2-20}$-alkoxyalkyl, $C_{6-14}$-aryl, $C_{7-20}$-alkylaryl, $C_{7-20}$-aralkyl, $C_{1-20}$-alkoxy, hydroxy, $C_{1-20}$-hydroxyalkyl, amino, $C_{1-20}$-alkylamino, $C_{2-20}$-dialkylamino, $C_{2-12}$-alkenylamino, $C_{3-8}$-cycloalkylamino, arylamino, diarylamino, aryl-$C_{1-8}$-alkylamino, halogen, mercapto, $C_{2-20}$-alkenyloxy, $C_{3-8}$-cycloalkoxy, aryloxy and/or $C_{2-8}$-alkoxycarbonyl, by reacting nitriles of the formula (III)

   (III)

with hydrogen at from 20 to 250° C. and pressures of from 60 to 350 bar in the presence of an Rh-containing catalyst comprising from 0.1 to 5% by weight, based on the total weight of the catalyst, of Rh on a support selected from the group consisting of activated carbon, silicon carbide and metal oxides, to give mixtures of primary amines of the formula (I)

   (I)

and secondary amines of the formula (II)

   (II)

and returning at least part of the primary amines separated from the mixtures obtained to the reaction.

2. A process as claimed in claim 1, wherein the amount of primary amines returned to the reaction is selected so that it corresponds essentially to the amount of primary amines present after the reaction.

3. A process as claimed in claim 1, wherein the catalyst contains from 0.3 to 3% by weight of Rh as the only active component.

4. A process as claimed in claim 1, wherein the support is $\gamma$-$Al_2O_3$ or $ZrO_2$.

5. A process as claimed in claim 1, wherein X is linear $C_{1-6}$-alkyl having up to 2 substituents.

6. A process as claimed in claim 5, wherein the substituents are $C_{2-12}$-dialkylamino or OH.

7. A process as claimed in claim 6, wherein the nitrile of the formula (III) is 3-(dimethylamino)propionitrile (DMAPN) and is converted into a mixture of bis(3-(dimethylamino)propyl)amine (bis-DMAPN) and

TABLE 1

| Feed | | | | Output | | | |
| --- | --- | --- | --- | --- | --- | --- | --- |
| DMAPN [g/h] | DMAPA [g/h] | DMAPN [g/h] | DMAPA [g/h] | DMAPN [g/h] | DMAPA [g/h] | Bis-DMAPA [g/h] | Output–input DMAPA [g/h] |
| 19.0 | 20.3 | 48 | 52 | 0.23 | 18.9 | 18.8 | −1.4 |
| 27.3 | 12.5 | 69 | 31 | 0.44 | 12.6 | 24.0 | 0.1 |
| 37.9 | 4.7 | 89 | 11 | 0.14 | 10.6 | 27.9 | 5.9 |

We claim:

1. A process for preparing secondary amines of the formula (II)

   (II)

where 3-(dimethylamino)propylamine (DMAPA), with bis-DMAPA being isolated as product and at least part of the DMAPA formed being returned to the reaction.

* * * * *